US008114445B2

(12) United States Patent
Hastings

(10) Patent No.: US 8,114,445 B2
(45) Date of Patent: Feb. 14, 2012

(54) DIETARY SUPPLEMENT FOR PROMOTING WELLNESS AND WEIGHT LOSS AND METHODS OF ADMINISTERING THE SAME

(75) Inventor: Carl W. Hastings, Wildwood, MO (US)

(73) Assignee: Reliv International inc., Chesterfield, MO (US)

( * ) Notice: Subject to any disclaimer, the term of this patent is extended or adjusted under 35 U.S.C. 154(b) by 16 days.

(21) Appl. No.: 12/613,443

(22) Filed: Nov. 5, 2009

(65) Prior Publication Data
US 2010/0119498 A1 May 13, 2010

Related U.S. Application Data

(60) Provisional application No. 61/112,400, filed on Nov. 7, 2008.

(51) Int. Cl.
*A61K 36/00* (2006.01)
(52) U.S. Cl. ...................................................... 424/725
(58) Field of Classification Search .......................... None
See application file for complete search history.

(56) References Cited

U.S. PATENT DOCUMENTS

| | | | |
|---|---|---|---|
| 3,436,407 A | 4/1969 | Masquelier | |
| 4,698,360 A | 10/1987 | Masquelier | |
| 5,720,956 A | 2/1998 | Rohdewald | |
| 6,136,339 A | 10/2000 | Gardiner | |
| 6,372,266 B1 | 4/2002 | Suzuki et al. | |
| 6,784,206 B2 | 8/2004 | Udell et al. | |
| 7,071,229 B2 | 7/2006 | Takayama et al. | |
| 7,375,111 B2 | 5/2008 | Weber et al. | |
| 7,425,571 B2 | 9/2008 | Gadde et al. | |
| 2005/0256178 A1* | 11/2005 | Eggersdorfer et al. | 514/393 |
| 2006/0269617 A1* | 11/2006 | Giampapa | 424/646 |
| 2006/0270650 A1* | 11/2006 | MacNeil et al. | 514/210.01 |
| 2006/0286182 A1* | 12/2006 | Patel | 424/739 |
| 2007/0155657 A1* | 7/2007 | Kojima et al. | 514/6 |
| 2008/0193603 A1 | 8/2008 | Hayes et al. | |
| 2008/0306154 A1* | 12/2008 | Svensson et al. | 514/560 |
| 2009/0233995 A1* | 9/2009 | Lautt | 514/440 |
| 2009/0252758 A1* | 10/2009 | Mazed et al. | 424/195.17 |
| 2010/0247501 A1* | 9/2010 | Ikeda | 424/93.51 |
| 2011/0064833 A1* | 3/2011 | Patell et al. | 424/739 |

OTHER PUBLICATIONS

DW ACC 2005-769689, Nov. 2005, Derwent or WO 2, Takagaki.*
DW ACC 2007-552560, Jul. 2007, Derwent or JP 2, Takahashi.*
"Alpha-Lipoic Acid," Retrieved from the Internet on Sep. 19, 2007: URL:http://www.umm.edu/altmed/articles/alpha-lipoic-000285.htm.
"Alpha-Lipoic Acid," PRD Health, Retrieved from the Internet on Sep. 19, 2007: URL:http://www.pdrhealth.com/drug_info/nmdrugprofiles/nutsupdrugs/alp_0159.shtml.
"Efficacy of Vijayasar (Pterocarpus Marsupium) in the Treatment of Newly Diagnosed Patients with Type 2 Diabetes Mellitus: A Flexible Dose Double-Blind Multicenter Randomized Controlled Trial," *Diabetologia Croatica*, 34(1):13-20 (2005).

"GlucoHelp™ for Healthy Blood Glucose Levels," (2005).
"Glutathione: Description," Retrieved from the Internet on Sep. 19, 2007: URL:http://www.pdrhealth.com/drug_info/nmdrugprofiles/nutsupdrugs/glu_0126.shtml.
"New Study Discovers How Pycnogenol Lowers Blood Glucose Levels in Type 2 Diabetes," Medical New Today, Retrieved from the Internet on Sep. 19, 2007: URL:http://www.medicalnewstoday.com/printerfriendlynews.php?newid=62607.
"Pycnogenol (*Pinus pinaster* ssp. atlantica)," Retrieved from the Internet on Sep. 19, 2007: URL:http://www.nlm.nih.gov/medlineplus/print/druginfo/natural/patient-pycnogenol.html.
"Pycnogenol for Diabetes Control," Retrieved from the Internet on Sep. 19, 2007: URL:http://www.diabeteshealth.com/read/2007/02/01/4977.html.
"Pycnogenol Lowers Blood Glucose Levels," Retrieved from the Internet on Sep. 19, 2007: URL:http://www.quantumhealth.com/news/pycnogenol_lowers_blood_glucose.html.
"Pycnogenol Lowers Blood Sugar Levels in Type 2 Diabetes," Retrieved from the Internet on Sep. 19, 2007: URL:http://www.nutraingredients.com/news/printNewBis.asp?id=55609.
"Pycnogenol's Latest Bragging Rights," Retreived from the Internet on Sep. 19, 2007: URL:http://www.diabeteshealth.com/read/2007/04/15/5094.html.
"Pycnogenol Proves Itself to be a Player in Diabetes Treatment," Retrieved from the Internet on Sep. 19, 2007: URL:http://www.diabeteshealth.com/read/2007/02/014977.html.
"Vanadyl Sulphate (Known as Vanadium, Vanadyl, Vanadyl Sulphate)," Retreived from the Internet on Sep. 19, 2007: URL:http://www.nutriline.org/article/113.
Axelrod, "Omega-3 Fatty Acids in Diabetes Mellitus. Gift from the Sea?" *Diabetes*, 38(5):539-543(1989). Abstract Only.
Banerjee et al., "In vitro Study of Antioxidant Activity of Syzygium cumini Fruit," Pharmacognosy Research Laboratory, Departmetn of Botany, University of Calcutta (2004). Abstract Only.
Borcea et al., "Alpha-Lipoic Acid Decreases Oxidative Stress Even in Diabetic Patients with Poor Glycemic Control and Albuminuria," *Free Radic. Biol. Med.*, 26(11-12):1495-1500 (1999).
Bornet et al., "Glycemic Response to Foods: Impact on Satiety and Long-Term Weight Regulation," *Appetite*, 49:535-553 (2007).
Bouche et al., "Five-week, Low-glycemic Index Diet Decreases Total Fat Mass and Improves Plasma Lipid Profile in Moderately Overweight Nondiabetic Men," *Diabetes Care*, 25:822-828 (2002).
Brand-Miller et al., "Carbohydrates—the Good, the Bad and the Whole Grain," *Asia Pac. J. Clin. Nutr.*, 17 Suppl (1):16-19 (2008).
Brand-Miller et al., "Glycemix Index and Obesity," *Am. J. Clin. Nutr.*, 76:281S-285S (2002).

(Continued)

*Primary Examiner* — Christopher R Tate
*Assistant Examiner* — Randall Winston
(74) *Attorney, Agent, or Firm* — Marshall, Gerstein & Borun LLP

(57) ABSTRACT

Disclosed herein are dietary supplements for promoting wellness and weight loss in a subject. In one aspect, the method includes administering to a subject whom wishes to lose weight a dietary supplement containing an extract product of *Salacia*, an extract product of *Lagerstroemea speciosa*, an extract product of French maritime pine bark, an extract product of *Pterocarpus marsupium*, and an extract product of *Syzygium cumini*, said composition being administered in an amount effective to promote wellness and weight loss in the subject.

38 Claims, 2 Drawing Sheets

OTHER PUBLICATIONS

Cerielo et al., "Hyperglycemia Counterbalances the Antihypertensive Effect of Gluthathione in Diabetic Patients: Evidence Linking Hypertension and Glycemia through the Oxidative Stress in Diabetes Mellitus," *J. Diabetes Complications*, 11(4).250-255 (1997). Abstract Only.

Cohen et al., "Oral Vanadyl Sulfate Improves Hepatic and Peripheral Insulin Sensitivity in Patients with Non-Insulin-dependent Diabetes Mellitus," *J. Clin. Invest.*, 95:2501-2509 (1995).

Collene et al., "Effects of a Nutritional Supplement Containing Salacia Oblonga Extract and Insulinogenic Amino Acids on Postprandial Glycemia, Insulinemia, and Breath Hydrogen Responses in Healthy Adults," *Nutrition*, 21:848-854 (2005).

Cusi et al., "Vanadyl Sulfate Improves Hepatic and Muscle Insulin Sensitivity in Type 2 Diabetes," *J. Clin. Endo. Metab.*, 86(3):1410-1416 (2007).

De Caterina et al., "n-3 Fatty Acids in the Treatment of Diabetic Patients," *Diabetes Care*, 30(4)1 012-1026 (2007).

Deocaris et al., "Hypoglycemic Activity of Irradiated Banaba (*Lagerstroemia speciosa* Linn.) eaves," *J. Appl. Sci. Res.*, 1(1):95-98 (2005).

Dhanabal et al., "Hypoglycemic Activity of *Pterocarpus marsupium* Roxb.," *Phytother Res.*, 20:4-8 (2006).

Fukushima et al., "Effect of Corosolic Acid on Postchallenge Plasma Glucose Levels," *Diabetes Res. Clin. Pract.*, 73:174-177 (2006).

Grundy et al., "Definition of Metabolic Syndrome, Report of the National Heart, Lung, and Blood Instiute/American Heart Association Conference on Scientific Issues Related to Definition," *Circulation*, 109:433-438 (2004).

Halberstam et al., "Oral Vanadyl Sulfate Improves Insulin Sensitivity in NIDDM but not in Obese Nondiabetic Subjects," *Diabetes*, 45(5):659-666 (1996).

Heacock et al., "Effects of a Medical Food Containing an Herbal Alpha-Glucosidase Inhibitor on Postprandial Glycemia and Insulinernia in Healthy Adults," *J. Am. Diet Assoc.*, 105:65-71 (2005).

Jacob et al., "The Antioxidant Alpha-Lipoic Acid Enhances Insulin-stimulated Glucose Metabolism in Insulin-Resistant Rat Skeletal Muscle," *Diabetes*, 45:1024-1029 (1996). Abstract Only.

Jayawardena et al., "A Double Blind Randomised Placebo Controlled Cross Over Study of a Herbal Preparation Containing *Salacia reticulate* in the Treatment of Type 2 Diabetes," *J. Ethnopharm.*, 97(2):215-218 (2005). Abstract Only.

Judy et al., "Antidiabetic Activity of a Standardized Extract (Glucosol™) From *Lagerstroemia speciosa* Leaves in Type II Diabetics. A Dose-Dependence Study," J. Ethnopharm., 87(1):115-117 (2003). Abstract Only.

Kakuda et al., "Hypoglycemic Effect of Extracts from *Lagerstroennia speciosa* L. Leaves in Genetically Diabetic KK-AY Mice," *Biosci. Biotechnol. Biochem.*, 60(2):204-208 (1996).

Kamenova, "Improvement of Insulin Sensitivity in Patients with Type 2 Diabetes Mellitus After Oral Administration of Alpha-Lipoic Acid," *Hormones (Athens)*, 5:251-258 (2006).

Kim et al., "The Water-Soluble Extract of Chicory Reduces Glucose Uptake from the Perfused Jejunum in Rats1,2," *J. Nut.*, 126:2236-2242 (1996).

Kishi et al., "α-Lipoic Acid: Effect on Glucose Uptake, Sorbitol Pathway, and Energy Metabolism in Experimental Diabetic Neuropathy," *Diabetes*, 48:2045-2051 (1999).

Klein et al., "Antidiabetes and Anti-Obesity Activity of *Lagerstroemia speciosa*," *eCAM Advance Access*, pp. 1-7 (2007).

Landgraf-Leurs et al., "Pilot Study of Omega-3 Fatty Acids in Type I Diabetes Mellitus," *Diabetes Care*, 39:369-375 (1990). Abstract Only.

Latest News from Indena, "Madeglucyl™, the Natural Way to Maintain Healthy Blood Sugar Levels," (2005).

Laube, "Acarbose," *Clin. Drug Invest.*, 22:141-156 2002.

Liu et al., "An Extract of Lagerstroemia speciosa L. has Insulin-Like Glucose Uptake-Stimulatory and Adipocyte Differentiation-Inhibitory Activities in 3T3-L1 Cells," *J. Nut.*, 131:2242-2247 (2001).

Liu et al., "Antidiabetic Effect of Pycnogenol French Maritime Pine Bark Extract in Patients with Diabetes Type II," *Life Sci.*, 75(21):2505-2513 (2004). Abstract Only.

Liu et al., "French Maritime Pine Bark Extract Pycnogenol Dose-Dependently Lowers Glucose in Type 2 Diabetic Patients," *Diabetes Care*, 27(3):839 (2004).

Malasanos et al., "Biological Effects of Omega-3 Fatty Acids in Diabetes Mellitus," *Diabetes Care*, 14(12):1160-1179 (1991). Abstract Only.

Mayer, "Glucostatic Mechanism of the Regulation of Food Intake," *New England J. Med.*, 249:13-16 (1953).

Mayo Clinic, "Antioxidant Alpha Lipoic Acid (ALA) Significantly Improves Symptoms of Diabetic Neuropathy," Retrieved from the Internet on Sep. 19, 2007: URL:http:www.mayoclinic.org/news2003-rst/1733.html.

McLennan et al., "Changes in Hepatic Glutathione Metabolism in Diabetes," *Diabetes*, 40(3):344-348 (1991).

Midaoui et al., "Prevention of Hypertension, Insulin Resistance, and Oxidative Stress by α-Lipoic Acid," *Hypertension*, 39:303-307 (2002).

Montori et al., "Fish Oil Supplementation in Type 2 Diabetes: A Quantitative Systematic Review," *Diabetes Care*, 23(9):1407-1415 (2000). Abstract Only.

Nosari et al., "Use of Omega-3 in Diabetic Patients," *Clin. Ter.*, 144(3):213-221 (1994). Abstract Only.

Pederson et al., "Long-term Effect of Vanadyl Treatment on Streptozocin-Induced Diabetes in Rats," Diabetes, 45(5):659-666 (1996). Abstract Only.

Pelikanova et al., "Metabolic Effects of Omega-3 Fatty Acids in Type 2 (Non-Insulin-Dependent) Diabetic Patients," *Ann. N.Y. Acad. Sci.*, 683:272-278 (1993). Abstract Only.

Penna et al., "Acarbose in Obese Patients with Polycystic Ovarian Syndrome: A Double-Blind, Randomized, Placebo-Controlled Study," *Hum. Reprod.*, 20:2396-2401 (2005).

Popp-Snijders et al., "Dietary Supplementation of Omega-3 Polyunsaturated Fatty Acids Improves Insulin Sensitivity in Non-Insulin-Dependent Diabetes," Diabetes Res., 4(3):141-147 (1987). Abstract Only.

Purnell et al., "Weight Effect of Current and Experimental Drugs for Diabetes Mellitus: From Promotion to Alleviation of Obesity," *Treat Endocrinol.*, 2:33-47 (2003).

Pycnogenol®, "About Pycnogenol®: Pycnogenol® is a Water Extract from the Bark of French Maritime Pine Grown as a Mono-Species Forest . . .," (2006).

Pycnogenol®, "Frequently Asked Questions," (2006).

Ramanadham et al., "Oral Vanadyl Sulfate in Treatment of Diabetes Mellitus in Rats," AJP—Heart and Circulatory Physiology, 257(3):904-H911 (1989). Abstract Only.

Rao et al., "Effect of Oral Administration of Bark Extracts of *Pterocarpus Santalinus* L. on Blood Glucose Level in Experimental Animals," *J. Ethnopharm.*, 74(1):69-74 (2001). Abstact Only.

Jacob et al., "Oral Administration of RAC-Alpha-Lipoic Acid Modulates Insulin Sensitivity in Patients with Type-2 Diabetes Mellitus: A Placebo-Controlled Pilot Trial," *Free Radic. Biol. Med.*, 27(3-4):309-314 (1999). Abstract Only.

Sakamaki et al., "Significance of Glutathione-Dependent Antioxidant System in Diabetes-Induced Embryonic Malformations," *Diabetes*, 48:1138-1144 (1999).

Schefer et al., "Oligomeric Procyanidins of French Maritime Pine Bark Extract (Pycnogenol®) Effectively Inhibit Alpha-Glucosidase," *Diabetes Res. Clin. Pract.*, 77:41-46 (2007).

Teixeira et al., "Skeels in the Treatment of Type 2 Diabetes: Results of a Randomized, Double-Blind, Double-Dummy, Controlled Trial," *Diabetes Care*, 27:3019-3020 (2004).

Teixeira et al., "The Effect of *Syzgium cumini* (L,) Skeels on Post-Prandial Blood Glucose Levels in Non-Diabetic Rats and Rats with Streptozotocin-Inducted Diabetes Mellitus," *J. Ethnopharacol.*, 56(3):209-213 (1997).

Thompson et al., "Studies of Vanadyl Sulfate as a Glucose-Lowering Agent in STZ-Diabetic Rats," *Biochem. Biophys. Res. Comm.*, 197(3):1549-1555 (1993).

Total Health Special Report, "Pycnogenol® French Maritime Pine Bark," (2007). Available at URL:http://www.totalhealthmagazine.com.

Venn et al., "Glycemic Index and Glycemic Load: Measurement Issues and Their Effect on Diet-Disease Relationships," *Eur. J. Clin. Nutr.*, 61 Supp. (1):122-131 (2007).

Warren et al., "Low Glycemic Index Breakfasts and Reduced Food Intake in Preadolescent Children," *Pediatrics*, 112:414-419 (2003).

Williams et al., "Extract of *Salacia oblonga* Lowers Acute Glycemia in Patients with Type 2 Diabetes," *Am. J. Clin. Nutr.*, 86(1)124-130 (2007). Abstract Only Wolf et al., "Safety Evaluation of an Extract from *Salacia oblonga*," *Food Chem. Toxicol.*, 41(6):867-874 (2003). Abstract Only Ziegler et al., "Treatment of Symptomatic Diabetic Polyneuropathy with the Antioxidant α-Lipoic Acid," *Diabetes Care*, 22(8)1296-1301 (1999).

Third Party Observation under section 37.1 of the Patent Act of Canada filed in corresponding Canadian Patent Application No. 2,684,853, dated Jul. 7, 2011.

* cited by examiner

DIETARY SUPPLEMENT FOR PROMOTING WELLNESS AND WEIGHT LOSS AND METHODS OF ADMINISTERING THE SAME

CROSS REFERENCE TO RELATED APPLICATION

The benefit under 35 U.S.C. §119(e) of U.S. provisional patent application Ser. No. 61/112,400, filed Nov. 7, 2008, the entire disclosure of which is incorporated herein by reference, is hereby claimed.

FIELD OF THE INVENTION

The invention relates to dietary supplements for promoting wellness and weight loss, and methods of administering the same.

BACKGROUND OF THE INVENTION

Metabolic syndrome is the collective presence in a subject of risk factors such as abdominal obesity, atherogenic dyslipidemia, raised blood pressure, insulin resistance, glucose intolerance, proinflammatory conditions, and prothrombotic conditions. See Grundy, et al., *Circulation,* 109(3): 433-38 (2004). When one or more, particularly two or more, of such risk factors are present, the subject has an increased risk for a variety of diseases including diabetes, heart disease, and/or stroke. Subjects having metabolic syndrome are also susceptible to other conditions such as polycystic ovary syndrome, fatty liver, cholesterol gallstones, asthma, sleep disturbance, and some forms of cancer.

Most practitioners consider weight reduction to be a primary therapy for treating metabolic syndrome. Weight reduction is also considered to be an effective therapy for treating obesity and obesity-related disorders including but not limited to type II diabetes and hypercholesteremia. Body mass index (BMI) is generally used to determine whether a subject is obese. BMI is calculated as weight (kg)/height (m$^2$). For adults over the age of 20, a BMI below 18.5 is considered underweight, a BMI in a range of 18.5 to 24.9 is considered normal, a BMI in a range of 25.0 to 29.9 is considered overweight, and a BMI in a range of 30.0 and above is considered obese.

In view of the foregoing, dietary supplements that promote weight loss are significant for health and wellness in general.

SUMMARY OF THE INVENTION

The disclosed dietary supplements and methods of administering the same can be used to treat subjects whom are obese, overweight, or simply wish to lose weight. In addition, the disclosed dietary supplements and methods of administering the same can be used to treat subjects having elevated fasting blood glucose levels, or fasting blood glucose levels approaching elevated levels.

In one aspect, a dietary supplement for promoting wellness and weight loss in a subject includes an extract product of *Pterocarpus marsupium* and an extract product of *Syzygium cumini*. In a refinement, the dietary supplement further comprises at least one of alpha lipoic acid, fatty acids (particularly omega 3 fatty acids), and coenzyme Q10.

In a related aspect, a method for promoting wellness and weight loss in a subject includes administering to a subject a dietary supplement that includes an extract product of *Pterocarpus marsupium*, and an extract product of *Syzygium cumini*, said supplement being administered in an amount effective to promote wellness and weight loss in the subject. In a refinement, the dietary supplement further comprises at least one of alpha lipoic acid, fatty acids (particularly omega 3 fatty acids), and coenzyme Q10.

In yet another aspect, a dietary supplement for promoting wellness and weight loss in a subject includes an extract product of *Salacia*, an extract product of *Lagerstroemea speciosa*, an extract product of French maritime pine bark, an extract product of *Pterocarpus marsupium*, and an extract product of *Syzygium cumini*. In a refinement, the dietary supplement further comprises at least one of alpha lipoic acid, fatty acids (particularly omega 3 fatty acids), and coenzyme Q10.

In a related aspect, a method for promoting wellness and weight loss in a subject includes administering to a subject a dietary supplement that includes an extract product of *Salacia*, an extract product of *Lagerstroemea speciosa*, an extract product of French maritime pine bark, an extract product of *Pterocarpus marsupium*, and an extract product of *Syzygium cumini*, said supplement being administered in an amount effective to promote wellness and weight loss in the subject. In a refinement, the dietary supplement further comprises at least one of alpha lipoic acid, fatty acids (particularly omega 3 fatty acids), and coenzyme Q10.

In another aspect, a dietary supplement for promoting wellness and lowering of fasting blood glucose level in a subject includes an extract product of *Pterocarpus marsupium* and an extract product of *Syzygium cumini*. In a refinement, the dietary supplement further comprises at least one of alpha lipoic acid, fatty acids (particularly omega 3 fatty acids), and coenzyme Q10.

In a related aspect, a method for promoting wellness and lowering of fasting blood glucose level in a subject includes administering to a subject a dietary supplement that includes an extract product of *Pterocarpus marsupium*, and an extract product of *Syzygium cumini*, said supplement being administered in an amount effective to promote wellness and lowering of fasting blood glucose level in the subject. In a refinement, the dietary supplement further comprises at least one of alpha lipoic acid, fatty acids (particularly omega 3 fatty acids), and coenzyme Q10.

In a still further aspect, a dietary supplement for promoting wellness and lowering of fasting blood glucose level in a subject includes an extract product of *Salacia*, an extract product of *Lagerstroemea speciosa*, an extract product of French maritime pine bark, an extract product of *Pterocarpus marsupium*, and an extract product of *Syzygium cumini*. In a refinement, the dietary supplement further comprises at least one of alpha lipoic acid, fatty acids (particularly omega 3 fatty acids), and coenzyme Q10.

In a related aspect, a method for promoting wellness and lowering of fasting blood glucose level in a subject includes administering to a subject a dietary supplement that includes an extract product of *Salacia*, an extract product of *Lagerstroemea speciosa*, an extract product of French maritime pine bark, an extract product of *Pterocarpus marsupium*, and an extract product of *Syzygium cumini*, said composition being administered in an amount effective to promote wellness and lowering of fasting blood glucose level in the subject. In a refinement, the dietary supplement further comprises at least one of alpha lipoic acid, fatty acids (particularly omega 3 fatty acids), and coenzyme Q10.

BRIEF DESCRIPTION OF THE DRAWINGS

Objects, features, and advantages of the disclosed dietary supplements and methods of administering the same will become apparent upon reading the following description in conjunction with the following drawing figures.

DETAILED DESCRIPTION OF THE INVENTION

Figure 1:
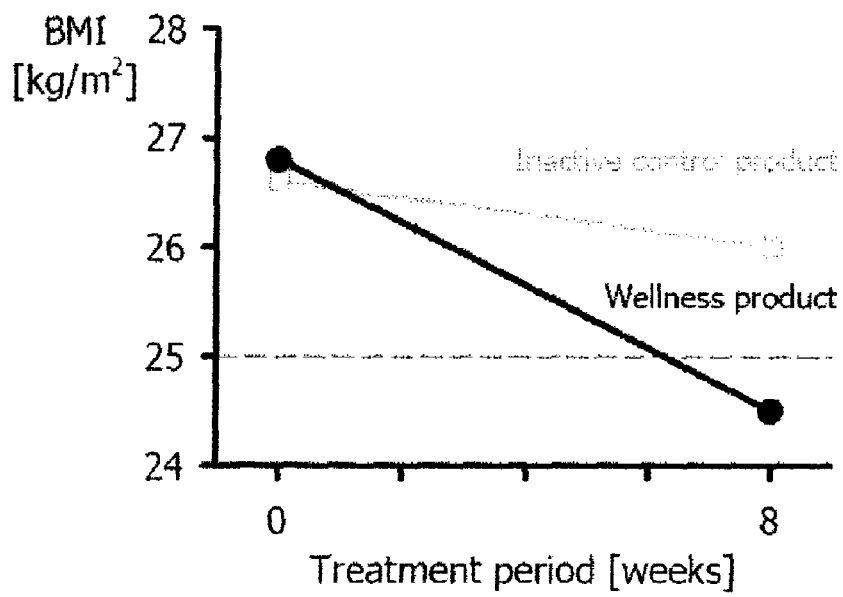
FIG. 1 is a graph showing how the body mass index (BMI) of (i) a group ("wellness product"), which received a dietary supplement for promoting wellness and weight loss in accordance with the invention, and (ii) a control group ("inactive control product"), which received an inactive control product, developed over an eight week treatment period, wherein the dotted line depicts the BMI of 25 kg/m$^2$, above which subjects are considered overweight.

Advantageously, the dietary supplements of the invention and methods of administering the same promote wellness and weight loss in a subject. Surprisingly, the dietary supplements can be administered to promote wellness and weight loss in a subject and, in some instances, can beneficially simultaneously lower the fasting blood glucose level of the subject. Thus, the dietary supplements of the invention are beneficial for individuals whom wish to lose weight, and are particularly efficacious for subjects whom are overweight or obese and have elevated fasting blood glucose levels. Further, the dietary supplements can advantageously reduce cellular/organ damage traditionally found in subjects whom experienced elevated blood glucose levels for substantial periods (e.g., damage to the heart, neuropathy, blindness, kidney failure, and other cellular and/or organ damage associated with elevated free radicals found in subjects having diabetes for significant time periods.) Thus, the subject supplements can be used for preventative, therapeutic, and even ameliorative applications.

In one aspect, a dietary supplement for promoting wellness and weight loss in a subject contains an extract product of *Pterocarpus marsupium* and an extract product of *Syzygium cumini*. In a related aspect, a method of promoting wellness and weight loss in a subject includes administering to a subject a dietary supplement containing an extract product of *Pterocarpus marsupium* and an extract product of *Syzygium cumini*, said supplement being administered in an amount effective to promote wellness and weight loss in the subject. In a refinement, the dietary supplement further comprises at least one of alpha lipoic acid, fatty acids (particularly omega 3 fatty acids), and coenzyme Q10.

In yet another aspect, a dietary supplement for promoting wellness and weight loss in a subject contains an extract product of *Salacia*, an extract product of *Lagerstroemea speciosa*, an extract product of French maritime pine bark, an extract product of *Pterocarpus marsupium*, and an extract product of *Syzygium cumini*. In a related aspect, a method for promoting wellness and weight loss in a subject comprises administering to a subject a dietary supplement comprising an extract product of *Salacia*, an extract product of *Lagerstroemea speciosa*, an extract product of French maritime pine bark, an extract product of *Pterocarpus marsupium*, and an extract product of *Syzygium cumini*, said supplement being administered in an amount effective to promote wellness and weight loss in the subject. In a refinement, the dietary supplement further comprises at least one of alpha lipoic acid, fatty acids (particularly omega 3 fatty acids), and coenzyme Q10.

In another aspect, a dietary supplement for promoting wellness and lowering of fasting blood glucose level in a subject contains an extract product of *Pterocarpus marsupium* and an extract product of *Syzygium cumini*. In a related aspect, a method for promoting wellness and lowering of fasting blood glucose level in a subject includes administering to a subject a dietary supplement containing an extract product of *Pterocarpus marsupium* and an extract product of *Syzygium cumini*, said supplement being administered in an amount effective to promote wellness and lowering of fasting blood glucose level in the subject. In a refinement, the dietary supplement further comprises at least one of alpha lipoic acid, fatty acids (particularly omega 3 fatty acids), and coenzyme Q10.

In still another aspect, a dietary supplement for promoting wellness and lowering of fasting blood glucose level in a subject contains an extract product of *Salacia*, an extract product of *Lagerstroemea speciosa*, an extract product of French maritime pine bark, an extract product of *Pterocarpus marsupium*, and an extract product of *Syzygium cumini*. In a related aspect, a method for promoting wellness and lowering of fasting blood glucose level in a subject comprises administering to a subject a dietary supplement containing an extract product of *Salacia*, an extract product of *Lagerstroemea speciosa*, an extract product of French maritime pine bark, an extract product of *Pterocarpus marsupium*, and an extract product of *Syzygium cumini*, said supplement being administered in an amount effective to promote wellness and lowering of fasting blood glucose level in the subject. In a refinement, the dietary supplement further comprises at least one of alpha lipoic acid, fatty acids (particularly omega 3 fatty acids), and coenzyme Q10.

The subject typically has one or more risk factors including being overweight or obese, insulin resistance, and glucose intolerance. Other risk factors including abdominal obesity, atherogenic dyslipidemia, raised blood pressure, proinflammatory conditions, and prothrombotic conditions, when present in a subject, can also warrant treatment with the dietary supplements and methods in accordance with the invention. Additionally, subjects whom simply wish to lose weight (but are not technically defined as being overweight and/or obese) may also benefit from receiving the dietary supplements for promoting wellness and weight loss—particularly if they exhibit relatively high fasting blood glucose levels (e.g. greater than 90 mg/dL, greater than 100 mg/dL, and/or greater than 126 mg/dL). In some embodiments, the subjects treated with the dietary supplements for promoting wellness and weight loss can be diabetic or pre-diabetic, as defined herein.

Body mass index (BMI) is generally used to determine whether a subject is overweight, or obese, as previously described. For adults over the age of 20, a BMI in a range of 25.0 to 29.9 is considered overweight, and a BMI in a range of 30.0 and above is considered obese.

"Insulin resistance" refers to a condition wherein a given concentration of insulin produces a less-than-expected biological effect. Insulin resistance generally refers to individuals requiring 200 or more units of insulin per day to attain glycemic control and prevent ketosis.

"Glucose intolerance" refers to a condition wherein an individual's blood sugar levels are higher than normal two hours after receiving oral glucose, but not high enough to be considered diabetic. Glucose intolerance generally refers to individuals whom can be classified as pre-diabetic.

As used herein, "abdominal obesity" refers to an individual having an increased waist circumference, and typically is present in a human male having a waist greater than about 40 inches and in a human female having a waist greater than about 35 inches. In an alternative aspect, abdominal obesity refers to individuals with body mass indices (i.e., [(individual's weight in pounds)/(individuals height in inches)$^2$ times 703]) exceeding about 25, more typically more than about 30.

"Raised blood pressure" refers to an individual having a systolic pressure exceeding about 130 mm Hg and/or a diastolic pressure exceeding about 85 mm Hg.

"Atherogenic dyslipidemia" refers to an elevated triglyceride concentration (serum concentration$\geq$150 mg/dL) and/or a depressed high-density lipoprotein cholesterol concentration (serum concentration$\leq$40 mg/dL for a male or $\leq$50 mg/dL for a female) in an individual.

As used herein, "proinflammatory conditions" refer to elevated concentrations of C-reactive protein, and "prothrombotic conditions" refer to increased plasminogen activator inhibitor (PAI)-1 and fibrinogen levels relative to healthy individuals, as is generally known. For example, administration of the compositions according to the invention can reduce various inflammatory markers including but not limited to Interleukin-6 (IL-6), Interleukin-8 (IL-8), and C-reactive protein (CRP), which are thought to have important interrelationships with traditional cardiovascular risk factors and higher than not normal concentrations of these markers are strongly correlated with the cellular/organ damage often found in subjects having elevated fasting blood glucose levels for significant time periods because of elevated free radical levels.

The subjects in need of the dietary supplement for promoting wellness and lowering of fasting blood glucose level generally have elevated fasting blood glucose levels and/or demonstrate insulin resistance and/or glucose intolerance. For example, the subjects can be pre-diabetic or diabetic. In some embodiments, the subjects whom can benefit from receiving dietary supplements for promoting wellness and lowering of fasting blood glucose level are also obese, overweight, or simply wish to lose weight.

Glucose levels are generally determined using a Fasting Plasma Glucose Test (FPG) or an Oral Glucose Tolerance Test (OGTT), but other tests may be used. With the FPG test, a fasting blood glucose level between 100 and 125 milligrams per deciliter (mg/dL) is indicative of pre-diabetes, and a fasting blood glucose level of 126 mg/dL or higher is indicative of diabetes. With the OGTT test, an individual's blood glucose level is measured two hours after oral administration of 75 grams of glucose. A two-hour blood glucose level between 140 mg/dL and 199 mg/dL is indicative of glucose intolerance or pre-diabetes. A two-hour glucose level at 200 mg/dL or higher is indicative of diabetes.

As used herein, the term "extract product" refers to any compound, any agent and/or mixtures thereof that is obtained, isolated, and/or derived from an extract of a plant material, including the extract itself. The term "plant material" refers to any plant material including, but not limited to, leaves, hark, stems, flowers, fruits, seeds, roots, and combinations thereof.

The dietary supplements of the invention generally include an extract product of *Pterocarpus marsupium*. The dietary supplements of the invention generally include at least about 0.50 weight percent (wt. %), between about 0.50 wt. % and 5.0 wt. %, and/or between about 1.0 wt. % and 3.0 wt. % of the extract product of *Pterocarpus marsupium*. Typically, a daily serving size of the dietary supplement is about 48 grams. When the dietary supplements of the invention are administered as a daily serving size of about 48 grams, the dietary supplements typically include at least about 0.2 grams, about 0.2 grams to about 2.5 grams, and/or about 0.5 grams to about 1.5 grams of the extract product of *Pterocarpus marsupium*. For example, the dietary supplements of the invention can include about 1.0 gram of the extract product of *Pterocarpus marsupium* per daily serving size of about 48 grams. *Pterocarpus marsupium*, of the family Leguminoceae, is a large tree that commonly grows in India and Sri Lanka. The extract product of *Pterocarpus marsupium* contains polyphenolic compounds such as, for example, diaryl propane derivatives, proterol, pterostilbene, pterosupin (a hydrochalcone), marsupsin (a benzofuranone), liquiritigenin (a flavonoid), and (–)-epicatechin. A suitable extract product of *Pterocarpus marsupium* is commercially available as Silbinol® (Sabinsa Corp., NJ).

The dietary supplements of the invention also generally contain an extract product of *Syzygium cumini*. The dietary supplements of the invention typically include at least about 0.50 wt. %, between about 0.50 wt. % and 7.5 wt. %, and/or between about 2.50 wt. % and 5.0 wt. % of the extract product of *Syzygium cumini* per daily serving. When the dietary supplements of the invention are administered as an about 48 gram daily serving size, the dietary supplements typically include at least about 0.2 grams, about 0.2 grams to about 3.5 grams, and/or about 1.0 gram to about 3.0 grams of the extract product of *Syzygium cumini*. For example, the dietary supplements of the invention can contain about 2.0 grams of the extract product of *Syzygium cumini* per daily serving size of about 48 grams. *Syzygium cumini* is also known as *Egenia jambolana* and *Syzygium jambolanum*, and commonly referred to as jamun, java plum, black plum, and Indian black berry. The extract product of *Syzygium cumini* is typically obtained from the seeds of *Syzygium cumini*, but may alternatively be obtained from any other suitable plant material. The extract product can be an alcohol extract of the seeds of *Syzygium cumini*, for example. The water-soluble portion of the alcoholic extract contains d-phenyl-glucosazone and a small amount of phenolic substance. The water-insoluble portion of the alcohol extract consisted of a soft resin, which contains a mixture of fatty acids, including, palmitic, stearic, oleic, and linoleic acids. A suitable extract product of *Syzygium cumini* is commercially available as Madeglucyl™ (Indena S.p.A., Milan, Italy).

The dietary supplements of the invention may include an extract product of *Salacia*. When an extract product of *Salacia* is present, the dietary supplements of the invention can include at least about 0.25 weight percent (wt. %), between about 0.25 wt. % and 2.5 wt. %, and/or between about 0.50 wt. % and 2.0 wt. % of the extract product of *Salacia*. When the dietary supplements of the invention are administered as a daily serving size of about 48 grams, the dietary supplements may include at least about 0.1 grams, about 0.1 grams to about 1.0 grams, and/or about 0.2 grams to about 0.6 grams of the extract product of *Salacia*. For example, the dietary supplements of the invention can contain about 0.5 grams of the extract product of *Salacia* per daily serving size of about 48 grams. *Salacia* is a genus of plants in the family Celastraceae. Suitable species of *Salacia* include *Salacia fimbrisepala*,

*Salacia mamba*, *Salacia miegei*, *Salacia oblonga*, *Salacia petenensis*, and *Salacia reticulatai*, and combinations thereof. Suitable extract products of *Salacia* are available in supplement form from a variety of sources.

The dietary supplements of the invention may include an extract product of *Lagerstroemia speciosa* L. When an extract product of *Lagerstroemia speciosa* L. is present, the dietary supplements of the invention can include at least about 0.01 wt. %, between about 0.01 wt. % and 0.50 wt. %, and/or between about 0.02 wt. % and 0.04 wt. % of the extract product of *Lagerstroemia speciosa* L. When the dietary supplements of the invention are administered as a daily serving size of about 48 grams, the dietary supplements may include at least about 0.005 grams, about 0.005 grams to about 0.03 grams, and/or about 0.01 grams to about 0.02 grams of the extract product of *Lagerstroemia speciosa* L. For example, the dietary supplements of the invention can contain about 0.016 grams of the extract product of *Lagerstroemia speciosa* L. per daily serving size of about 48 grams. *Lagerstroemia speciosa* L., commonly known as Crepe Myrtle or Banaba, is a Southeast Asian tree. The leaf extracts contain significant amounts of corosolic acid (2-a-hydroxyursolic acid) and tannins, including lagerstroemin. A suitable extract product of *Lagerstroemia speciosa* L. is commercially available as GlucoHelp™ (OptiPure, CA), which contains at least 18% corosolic acid.

The dietary supplements of the invention may also include an extract product of French maritime pine bark. When a French maritime pine bark extract product is present, the dietary supplements of the invention can include at least about 0.01 wt. %, between about 0.01 wt. % and 1.0 wt. %, and/or between about 0.05 wt. % and 0.15 wt. % of the extract product of French maritime pine bark. When the dietary supplements of the invention are administered as a daily serving size of about 48 grams, the dietary supplements typically include at least about 0.01 grams, about 0.01 grams to about 0.5 grams, and/or about 0.04 grams to about 0.08 grams of the extract product of French maritime pine bark extract. For example, the dietary supplements of the invention can include about 0.06 grams of the extract product of French maritime pine bark per daily serving size of about 48 grams. French maritime pine trees (*pinus pinaster* ssp. atlantica) grow on the coast of southwest France. The extract product of French maritime pine bark, includes a variety of bioflavonoids, such as, for example, catechin, epicatechin, proanythocyanidins such as taxitolin, and phenolic fruit acids such as ferulic acid and caffeic acid. A suitable extract product of French maritime pin bark is commercially available as Pycnogenol® (Horphag Research Ltd., UK).

The dietary supplements of the invention may further include alpha lipoic acid. The dietary supplements of the invention typically include at least about 0.25 wt. %, between about 0.25 wt. % and 2.5 wt. %, and/or between about 0.50 wt. % and 1.5 wt. %, of alpha lipoic acid. When the dietary supplements are administered as a daily serving size of about 48 grams, the dietary supplements typically include at least about 0.1 grams, about 0.1 grams to about 1.5 grams, and/or about 0.2 gram to about 0.6 grams of alpha lipoic acid. For example, the dietary supplements of the invention can include about 0.4 grams of alpha lipoic acid per daily serving size of about 48 grams. Alpha lipoic acid is a disulfide compound that is a cofactor in vital energy-producing reactions in the body. Sources of alpha lipoic acid include plant and animal sources, such as for example, spinach, broccoli, beef, and yeast. Alpha lipoic acid is also commercially available as a dietary supplement. A suitable commercially available alpha lipoic acid supplement is Ultra-Lipoic Forte (Westlake Laboratories, Inc., OH).

The dietary supplements of the invention may further include fatty acids. When fatty acids are included, the dietary supplements of the invention typically include at least about 0.50%, between about 0.50 wt. % and 10.0 wt. %, and/or between about 3.0 wt. % and 7.0 wt. % of fatty acids. When the dietary supplements of the invention are administered as a daily serving size of about 48 grams, the dietary supplements can include at least about 0.2 grams, about 0.2 grams to about 5.0 grams, and/or about 2.0 grams to about 4.0 grams of fatty acids. For example, the dietary supplements of the invention can include about 3.0 grams of fatty acid per daily serving size of about 48 grams. The dietary supplements of the invention can include saturated fatty acids, polyunsaturated fatty acids, and mixtures thereof. Examples of representative saturated fatty acids include, but are not limited to, butanoic acid, hexanoic acid, octanoic acid, decanoic acid, dodecanoic acid, tetradecanoic acid, hexadecanoic acid, octadecanoic acid, eicosanoic acid, docosanoic acid, and tetracosanoic acid. Examples of representative unsaturated fatty acids include, but are not limited to, myristoleic acid, palmitoleic acid, oleic acid, linoleic acid, linolenic acid, arachidonic acid, eicosapentaenoic acid, erucic acid, and docosahexaenoic acid. When fatty acids are included, the dietary supplements preferably contain omega-3 fatty acids, such as for example, α-linolenic acid (ALA), stearidonic acid (STD), eicosatrienoic acid (ETE), eicosatetraenoic acid (ETA), eicosapentaenoic acid (EPA), docosahexaenoic acid (DHA), docosapentaenoic acid (DPA), tetracosapentaenoic acid, and tetracosahexaenoic acid (nisinic acid). More preferably, the dietary supplement contains at least EPA and DHA. Sources of omega-3 fatty acids include, fish oils, flax (*Linum usitatissimum*) and its oils, chia, kiwifruit, perilla, lingoberry, camelina, purslane, black raspberry, butternuts, walnuts, pecans, hazel nuts, extracts and extract products isolated therefrom, and mixtures thereof. Omega 3 fatty acids are also commercially available in a supplement form from a variety of sources.

The dietary supplements of the invention can further include coenzyme Q10. When coenzyme Q10 is included, the dietary supplements of the invention can include at least about 0.01 wt. %, between about 0.01 wt. % and about 1.0 wt. %, and/or between about 0.05 wt. % and 0.2 wt. % of coenzyme Q10. When the dietary supplements of the invention are administered as a daily serving size of about 48 grams, the dietary supplements can include at least about 0.01 grams, about 0.01 grams to about 0.2 grams, and/or about 0.05 grams to about 0.1 grams of coenzyme Q10. For example, the dietary supplements of the invention can include about 0.08 grams of coenzyme Q10 per daily serving size of about 48 grams. Coenzyme Q10 catalyzes the formation and utilization of energy in human cells. Other suitable sources of coenzyme Q10 include pork heart, mackerel, herring, soybean and its oils, canola oil, peanut and its oils, chicken, beef sesame and its oils, and extract and extract products isolated therefrom.

The dietary supplements of the invention can also further include L-glutathione. When L-glutathione is included, the dietary supplements of the invention can include at least about 0.01 wt. %, between about 0.01 wt. % and 1.0 wt. %, and/or between about 0.05 wt. % and 0.15 wt. % of L-glutathione. When the dietary supplements of the invention are administered as a daily serving size of about 48 grams, the dietary supplements can include at least about 0.01 grams, about 0.01 to about 0.5 grams, and/or about 0.03 grams to about 0.07 grams of L-glutathione. For example, the dietary supplements of the invention can include about 0.05 grams of L-glutathione per daily serving size of about 48 grams. Sources of L-glutathione include fruits such as tomatoes, watermelon, grapefruit, oranges, preaches, and cantaloupe, vegetables, such as broccoli, cabbage, Brussel sprouts, cauliflower, kale, parsley, and extracts and extract products isolated from such fruits and vegetables. L-glutathione is also commercially available in supplement form from a variety of sources.

The dietary supplement can further include cinnamon. When cinnamon is included, the dietary supplements of the invention typically include at least about 0.2 wt. %, between about 0.2 wt. % and 1.5 wt. %, and/or between about 0.2 wt. % and 0.5 wt. % of cinnamon. When the dietary supplements of the invention are administered as a daily serving size of about 48 grams, the dietary supplements can include at least about 0.05 grams, about 0.05 to about 0.7 grams, and/or about 0.1 grams to about 0.25 grams of cinnamon. For example, the dietary supplements of the invention can include about 0.18 grams of cinnamon per daily serving size of about 48 grams. Cinnamon may be included for both its flavoring properties and its unexpected therapeutic affect in combination with other ingredients of the dietary supplements. Most commonly, cinnamon is obtained from the bark of the species *C. zeylanicum*.

The dietary supplements of the invention can further include soluble fiber. Suitable soluble fiber sources include but are not limited to oats, peas, beans, certain fruits, extracts, and extract products isolated therefrom, and mixtures thereof. Preferably, the soluble fiber is selected from inulin, guar gum, and combinations thereof. When inulin is included, the dietary supplements of the invention may include at least about 0.5 wt. %, between about 0.5 wt. % and 6.0 wt. %, and/or between about 2.0 wt. % and 4.0 wt. % of inulin. When the dietary supplements of the invention are administered as a daily serving size of about 48 grams, the dietary supplements can include at least about 0.2 grams, about 0.2 grams to about 3.0 grams, and/or about 1.0 grams to about 2.0 grams of inulin. For example, the dietary supplements of the invention can include about 1.6 grams of inulin per daily serving size of about 48 grams. When guar gum is included, the dietary supplements of the invention can include at least about 0.25 wt %, between about 0.25 wt. % and 2.5 wt. %, and/or between about 0.5 wt. % and 1.5 wt. % of guar gum. When the dietary supplements of the invention are administered as a daily serving size of about 48 grams, the dietary supplements can include at least about 0.1 grams, about 0.1 grams to about 1.0 grams, and/or about 0.3 grams to about 0.7 grams of guar gum. For example, the dietary supplements of the invention can include about 0.5 grams of guar gum per daily serving size of about 48 grams. Inulin can be obtained from chicory, onions, artichokes, bananas, asparagus, garlic, extracts and extract products isolated therefrom, and mixtures thereof. Suitable sources of inulin include elecampane, dandelion, wild yam, Jerusalem artichoke, chicory, jimaca, burdock, onion, garlic, agave, yacon, and extracts and extract products isolated therefrom. Guar gum is an extract product of guar beans (*cyamopsis tetragonolobus*). Soluble fiber sources, such as inulin and guar gum, are also commercially available in supplement form from a variety of sources.

The dietary supplements of the invention can further include vanadyl sulfate (including hydrates thereof). When vanadyl sulfate is included, the dietary supplements of the invention can include at least about 0.005 wt. %, between about 0.005 wt. % and 0.5 wt. %, and/or between about 0.01 wt. % and 0.03 wt. % of vanadyl sulfate. When the dietary supplements of the invention are administered as a daily serving size of about 48 grams, the dietary supplements can include at least about 0.002 grams, about 0.002 grams to about 0.2 grams, and/or about 0.005 grams to about 0.010 grams of vanadyl sulfate. For example, the dietary supplements of the invention can include about 0.008 grams of vanadyl sulfate hydrate per daily serving size of about 48 grams.

The dietary supplements of the invention can also include soy flour. When soy flour is included, the dietary supplements of the invention can include at least about 40 wt. %, between about 40 wt. % and about 95 wt. %, and/or between about 60 wt. % and 80 wt. % of soy flour. When the dietary supplements of the invention are administered as a daily serving size of about 48 grams, the dietary supplements include at least about 15 grams, about 15 grams to about 47 grams, and/or about 25 grams to about 45 grams of soy flour. For example, the dietary supplements of the invention can include about 35 grams of soy flour per daily serving size of about 48 grams.

Various natural or artificial flavoring components can also be included in the dietary supplements of the invention to mask or block extant flavors of several of the other components or otherwise flavor the dietary supplements of the invention. Suitable flavoring components include, for example, melon flavor, chocolate flavor, strawberry flavor, cherry flavor, vanilla cream flavor, honey flavor, French vanilla flavor, Chai flavor, and combinations thereof. Sweetening agents including but not limited to artificial sweeteners, such as aspartame, acesulfame-potassium, sugar substitutes, maltodextrin, fructose, various sweetness enhancers can also be included to flavor the dietary supplements of the invention. Conventional food supplement additives can also be included. Representative food supplement additives include, but are not limited to, citric acid, and emulsifiers such as lecithin and xanthan gum. Preferably, the lecithin is non-GMO soy lecithin.

The dietary supplements of the invention can be formulated as pharmaceutical compositions (e.g., an ethical drug), nutraceutical compositions (e.g., a dietary supplement), cosmeceuticals (e.g., a cosmetic product having biologically active ingredients), or as a food or beverage additive as defined by the U.S. Food and Drug Administration.

In the methods according to the invention, the dietary supplements can be administered by any known route of administration. The dietary supplements can be formulated for injection, oral, nasal, transdermal or other forms of administration. For example, the dietary supplements can be administered as a part of foods or beverages including, but not limited to, lozenges, gums, bars, shakes, drinks, and other processed or prepared foods. The dietary supplements can also be formulated as pills, capsules, tablets, powders, liquids, or other forms consistent with oral and/or injectable administration. In some embodiments, the dietary supplements are prepared using a non-toxic alcohol or an aqueous solution. Preferably, the dietary supplement is formulated to be mixed with water for oral administration.

In accordance with the methods of the invention, a typical treatment course includes administration of the dietary supplement in an amount effective to reduce the weight and/or the fasting glucose level of the subject. Administration of the dietary supplement is typically continued for a significant period of time. For example, the dietary supplement can be administered as multiple daily doses for significant periods of time, such as, four doses (e.g., cumulatively amounting to a daily serving size of about 48 grams) per day over two months or even indefinitely. Alternatively, the dietary supplement can be administered as a single daily dose (i.e., a single serving amounting to a daily serving size of about 48 grams) for significant periods of time, for example one dose per day over two months or even indefinitely. Where the administration of the dietary supplement includes multiple doses of the dietary supplement, the daily serving amount of the dietary supplement or the subject components thereof are typically divided equally among the doses. The dietary supplement can be administered to the subject at any time.

Of course, the foregoing are only exemplary treatment schedules, and other schedules are contemplated. In each case, the suitability of such schedules and the aforementioned modes of administration are determined by those skilled in the art, using routine procedures. For example, those skilled in the art will be able to take the information disclosed in the specification and optimize treatment regimes for human subjects based on clinical trials performed in accordance with the specification.

It will be appreciated that the dietary supplements of the invention and methods of administering the same are useful in the fields of human medicine and veterinary medicine. Thus, the subjects to be treated can be a mammal, preferably human, or other animal.

Example

The following example is provided to describe the invention in greater detail, and is intended to illustrate, not limit, the appended claims.

Subjects

Fifty overweight subjects with moderately elevated fasting blood glucose were randomly assigned in a single blind fashion to either receive a dietary supplement in accordance with the invention (the treatment group) or an inactive control product with substantially identical taste, color, and texture (the control group). The subjects were from San Valentino, Italy, where a typical diet contains excessive refined sugars and starches.

Inclusion criteria included a BMI of greater than about 25 kg/m$^2$ and a fasting blood glucose level of greater than 100 mg/dL. Exclusion criteria included a fasting blood glucose level higher than 160 mg/dL and any other metabolic or clinical conditions requiring medical or drug treatment. Severely handicapped people, individuals with psychiatric disorders including depression, pregnant or nursing women, and individuals who participated in another study less than 30 days before the start of treatment were also excluded.

The treatment group included 24 subjects, 14 men and 10 women, aged 30 to 60 years. The mean age of the treatment group was 42.3±8.3 years. The fasting blood glucose level of the subjects at recruitment ranged from 114 mg/dL to 160 mg/dL, with a mean value of 145.3 mg/dL±24.5 mg/dL.

The control group included 26 subjects, 15 men and 11 women, aged 30 to 58 years. The mean age of the control group was 43±7.1 years. The fasting blood glucose level of the subjects at recruitment ranged from 116 mg/dL to 158 mg/dL, with a mean value of 143.1 mg/dL±21 mg/dL.

The BMI, body weight, fasting blood glucose level, and HbA1c, were assessed upon recruitment to establish a baseline and again after 8 weeks of supplementation with either a dietary supplement in accordance with the invention or the inactive control product.

Treatment Regimen

Subjects were given a canister containing either a four week supply of a dietary supplement in accordance with the invention or an inactive control product. A second canister was given to the subjects upon return of the first canister after the first four weeks of treatment. Subjects consumed four servings of either a dietary supplement in accordance with the invention or an inactive control product during the day. Each serving contained about 12 grams of powder mixed with about 200 ml of water. Tables 1 and 2 show the composition per serving of the dietary supplement in accordance with the invention and the inactive control product. Subjects consumed the dietary supplement in accordance with the invention or the inactive control product six days a week (generally Monday through Saturday), replacing two meals a day with the dietary supplement or inactive control product. Subjects were allowed to have a dinner of their choice. The subjects were also allowed to consume the food of their choice one day a week, typically Sunday. However, the subjects were encouraged to have low calorie meals with limited amounts of carbohydrates. Subjects were also encouraged to exercise three times a day for a total of 60 minutes per day. Analysis of the canisters containing either the dietary supplement in accordance with the invention or the inactive control product returned after the initial four week supply was consumed suggested good compliance with the treatment regimen, with no more than two servings missed per week.

TABLE 1

Composition of the Dietary Supplement in Accordance with the Invention per Serving

| Ingredient | Grams |
| --- | --- |
| Non GMO Low Fat Soy Flour | 8.7185 |
| Non GMO, Lecithin | 0.1500 |
| Omega-3 Fish Oils (EPA/DHA) | 0.7500 |
| Madeglucyl ™ | 0.5000 |
| Inulin | 0.4000 |
| Silbinol ®, *Pterocarpus marsupium* 5% | 0.2500 |
| *Salacia* extract | 0.1200 |
| Guar Gum | 0.1200 |
| Xanthan Gum | 0.1200 |
| Alpha Lipoic Acid | 0.1000 |
| Flavoring | 0.5550 |
| Cinnamon, ground | 0.0450 |
| Sweetening agent | 0.0900 |
| Sweetening agent | 0.0300 |
| L-Glutathione | 0.0125 |
| Pycnogenol ® | 0.0150 |
| GlucoHelp ™ | 0.0040 |
| Coenzyme Q 10 | 0.0200 |
| Total Weight | 12.0000 |

TABLE 2

Composition of the Inactive Control Product per Serving

| Ingredient | Grams |
| --- | --- |
| Non GMO Low Fat Soy Flour | 8.780 |
| Non GMO, Sunflower Oil | 1.000 |
| Non GMO Corn Based Maltodextrin | 1.210 |
| Non GMO Corn Based Starch | 0.350 |
| Natural and Artificial Flavor | 0.580 |
| Cinnamon, ground | 0.044 |
| Sweetening agent | 0.094 |
| Total Weight | 12.058 |

Results

Referring to FIG. 1, the weight and BMI of the treatment group subjects decreased significantly as compared to the baseline and the control group. At recruitment, the average body weight in the treatment group was 88.5±4.4 kg, with an average BMI of 26.8±4.3 kg/m$^2$. After 8 weeks of receiving a dietary supplement in accordance with the invention, the average body weight of the treatment group decreased to 81.3±5.0 kg and the average BMI decreased to 24.5±4.9 kg/m$^2$. Thus, the average treatment group subject lost 7.2 kg within 8 weeks and achieved their optimal weight with a BMI <25.0 kg/m$^2$. No such significant weight loss was found in the control group, which demonstrated a drop in average body weight from 87±5.0 kg at recruitment to 85±4.3 kg, and a decrease in BMI of 26.6±5.0 kg/m² at recruitment to 25.99±4.3 kg/m². The dotted line in FIG. 1 depicts a BMI of 25 kg/m², above which people are considered overweight.

Figure 2:
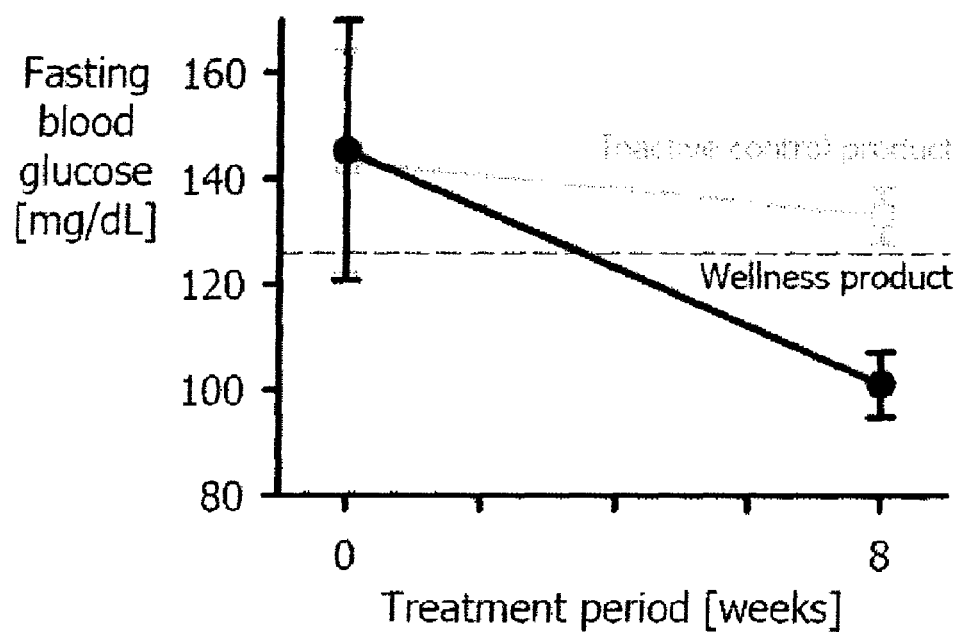
FIG. 2 is graph showing how the fasting blood glucose levels of (i) a group ("wellness product"), which received a dietary supplement for promoting wellness and lowering of fasting blood glucose level in accordance with the invention, and (ii) a control group ("inactive control product"), which received an inactive control product, developed over an eight week treatment period, wherein the dotted line depicts the 126 mg/dL (7 mmol/l) fasting glucose level threshold, above which subjects are considered diabetic.
Figure 3:
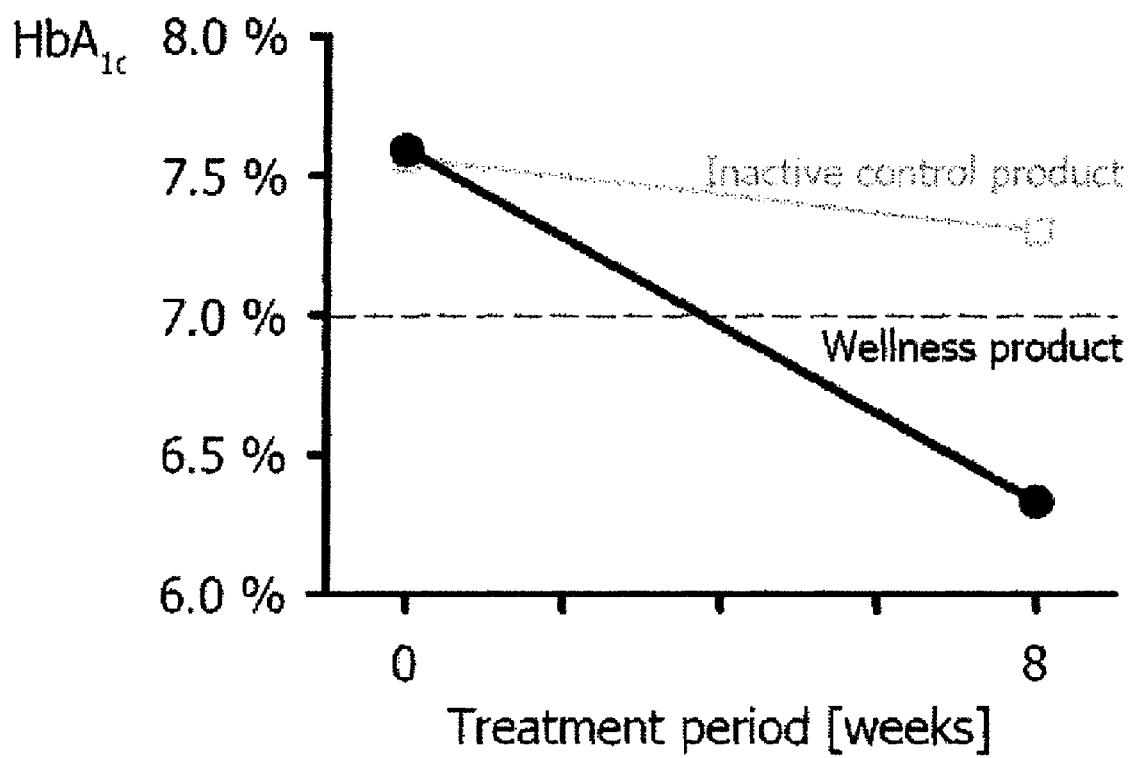
FIG. 3 is a graph showing how the percentage of glycosylated hemoglobin (HbA1c) of (i) a group ("wellness product"), which received a dietary supplement for promoting wellness and lowering of fasting blood glucose level in accordance with the invention, and (ii) a control group ("inactive control product"), which received an inactive control product, wherein the dotted line depicts the 7% threshold value, above which subjects are considered to have poor control of blood glucose levels.

Referring to FIG. 2, consumption of the dietary supplement in accordance with the invention was found to lower blood fasting glucose level by approximately 30.4%, i.e., from a baseline of 145.3±24.5 mg/dL to 101.1±6.2 mg/dL. The dotted line in FIG. 2 depicts the borderline 126 mg/dL fasting blood glucose level, above which subjects are considered diabetic. The fasting glucose level lowering of the treatment group was statistically significant as compared to the borderline 126 mg/dL fasting blood glucose level, as well as to the control group where the values decreased marginally from 143.1±21 mg/dL to 133.0±22 mg/dL. Referring to FIG. 3, the lowered fasting blood glucose of the treatment group subjects was confirmed by reduction of the HbA1c level, which decreased significantly to 6.33% as compared to the baseline of 7.59%. No significant HbA1c lowering was found in the control group, which decreased marginally from 7.56% to 7.3%. The dotted line in FIG. 3 depicts the 7% threshold value, above which subjects are considered to have poor control of blood glucose levels.

The dietary supplement in accordance with the invention was well tolerated, and no subjects dropped out of the trial. Standard clinical chemistry confirmed excellent tolerance of the exemplified dietary supplement as well as the inactive control product. There were no abnormal blood chemistries, complications, or other side effects observed in either the treatment group or the control group.

The invention is not limited to the embodiments described and exemplified above, but rather is capable of variation and modification without departure from the scope of the appended claims.

What is claimed is:

1. A method for promoting weight loss in a subject in need thereof, the method comprising:
   administering to a subject a dietary supplement comprising an extract product of *Salacia*, an extract product of *Lagerstroemea speciosa*, an extract product of French maritime pine bark, an extract product of *Pterocarpus marsupium*, and an extract product of *Syzygium cumini*, in amounts effective to promote weight loss in the subject.

2. The method of claim 1, wherein the dietary supplement further comprises a source of soluble fiber.

3. The method of claim 1, wherein the soluble fiber source is selected from the group consisting of inulin, guar gum, and combinations thereof.

4. The method of claim 1, wherein the dietary supplement further comprises cinnamon.

5. The method of claim 1, wherein the dietary supplement further comprises vanadyl sulfate.

6. The method of claim 1, wherein the dietary supplement further comprises L-Glutathione.

7. The method of claim 1, wherein the dietary supplement further comprises coenzyme Q10.

8. The method of claim 1, wherein the dietary supplement further comprises fatty acids.

9. The method of claim 8, wherein the fatty acids comprise omega 3 fatty acids.

10. The method of claim 1, wherein the dietary supplement further comprises alpha lipoic acid.

11. The method of claim 1, wherein the dietary supplement further comprises one or more of low fat soy flour, lecithin, xanthan gum, natural flavor, artificial flavor, and sweetening agents.

12. The method of claim 1, comprising administering the dietary supplement to the subject daily.

13. The method of claim 1, comprising administering a total serving of about 48 grams of the dietary supplement to the subject daily, wherein the total serving of the dietary supplement comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.2 grams to 2.5 grams, and the extract product of *Syzygium cumini* in a range of 0.2 grams to 3.5 grams.

14. The method of claim 1, wherein the dietary supplement comprises about 0.25 weight percent (wt. %) to about 2.5 wt. % of the extract product of *Salacia*; about 0.01% to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

15. The method of claim 1, further comprising mixing the dietary supplement with water prior to administering the dietary supplement to the subject.

16. A method for promoting lowering of fasting blood glucose level of a subject in need thereof, the method comprising:
   administering to a subject a dietary supplement comprising an extract product of *Salacia*, an extract product of *Lagerstroemea speciosa*, an extract product of French maritime pine bark, an extract product of *Pterocarpus marsupium*, and an extract product of *Syzygium cumini*, said composition being administered in amounts effective to promote lowering of fasting blood glucose level of the subject.

17. A dietary supplement for promoting weight loss in a subject, comprising:
   effective amounts of an extract product of *Salacia*, an extract product of *Lagerstroemea speciosa*, an extract product of French maritime pine bark, an extract product of *Pterocarpus marsupium*, and an extract product of *Syzygium cumini*.

18. The dietary supplement of claim 17, wherein a total serving of the dietary supplement has a weight of about 48 grams and comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.5 grams to 5.0 grams, and the extract product of *Syzygium cumini* in a range of 0.2 grams to 3.5 grams.

19. The dietary supplement of claim 17, wherein the dietary supplement comprises about 0.25 weight percent (wt. %) to about 2.5 wt. % of the extract product of *Salacia*; about 0.01 wt. % to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

20. The dietary supplement of claim 17, further comprising a soluble fiber source.

21. The dietary supplement of claim 20, wherein the soluble fiber source is selected from the group consisting of inulin, guar gum, and combinations thereof.

22. The dietary supplement of claim 17, further comprising cinnamon.

23. The dietary supplement of claim 17, further comprising vanadyl sulfate.

24. The dietary supplement of claim 17, further comprising L-Glutathione.

25. The dietary supplement of claim 17, further comprising coenzyme Q10.

26. The dietary supplement of claim 17, further comprising fatty acids.

27. The dietary supplement of claim 17, wherein the fatty acids comprises omega 3 fatty acids.

28. The dietary supplement of claim 17, further comprising alpha lipoic acid.

29. The dietary supplement of claim 17, further comprising one or more of low fat soy flour, lecithin, xanthan gum, natural flavor, artificial flavor, and sweetening agents.

30. A dietary supplement for promoting lowering of fasting blood glucose level of a subject, comprising
effective amounts of an extract product of *Salacia*, an extract product of *Lagerstroemea speciosa*, an extract product of French maritime pine bark, an extract product of *Pterocarpus marsupium*, and an extract product of *Syzygium cumini*.

31. A method for promoting wellness and weight loss in a subject, the method comprising:
administering to a subject a dietary supplement comprising an extract product of *Salacia*, an extract product of *Lagerstroemea speciosa*, an extract product of French maritime pine bark, an extract product of *Pterocarpus marsupium*, and an extract product of *Syzygium cumini*, the dietary supplement being administered in an amount effective to promote wellness and weight loss in the subject,
wherein the dietary supplement comprises about 0.25 weight percent (wt. %) to about 2.5 wt. % of the extract product of *Salacia*; about 0.01% to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

32. The method of claim 31, wherein a total serving of the dietary supplement has a weight of about 48 grams and comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.5 grams to 5.0 grams, and the extract product of *Syzygium cumini* in a range of 0.2 grams to 3.5 grams.

33. A method for promoting wellness and lowering of fasting blood glucose level of a subject, the method comprising:
administering to a subject a dietary supplement comprising an extract product of *Salacia*, an extract product of *Lagerstroemea speciosa*, an extract product of French maritime pine bark, an extract product of *Pterocarpus marsupium*, and an extract product of *Syzygium cumini*, said dietary supplement being administered in an amount effective to promote wellness and lowering of fasting blood glucose level of the subject,
wherein the dietary supplement comprises about 0.25 weight percent (wt. %) to about 2.5 wt. % of the extract product of *Salacia*; about 0.01% to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

34. The method of claim 33, wherein a total serving of the dietary supplement has a weight of about 48 grams and comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.5 grams to 5.0 grams, and the extract product of *Syzygium cumini* in a range of 0.2 grams to 3.5 grams.

35. A dietary supplement for promoting wellness and weight loss in a subject, comprising:
an extract product of *Salacia*, an extract product of *Lagerstroemea speciosa*, an extract product of French maritime pine bark, an extract product of *Pterocarpus marsupium*, and an extract product of *Syzygium cumini*,
wherein the dietary supplement comprises about 0.25 weight percent (wt. %) to about 2.5 wt. % of the extract product of *Salacia*; about 0.01% to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

36. The dietary supplement of claim 35, wherein a total serving of the dietary supplement has a weight of about 48 grams and comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.5 grams to 5.0 grams, and the extract product of *Syzygium cumini* in a range of 0.2 grams to 3.5 grams.

37. A dietary supplement for promoting wellness and lowering of fasting blood glucose level of a subject, comprising:
an extract product of *Salacia*, an extract product of *Lagerstroemea speciosa*, an extract product of French maritime pine bark, an extract product of *Pterocarpus marsupium*, and an extract product of *Syzygium cumini*,
wherein the dietary supplement comprises about 0.25 weight percent (wt. %) to about 2.5 wt. % of the extract product of *Salacia*; about 0.01% to about 0.5 wt. % of the extract product of *Lagerstroemea speciosa*; about 0.01 wt. % to about 1.0 wt. % of the extract product of French maritime pine bark; about 0.5 wt. % to about 5.0 wt. % of the extract product of *Pterocarpus marsupium*; and about 0.5 wt. % to about 7.5 wt. % of the extract product of *Syzygium cumini*.

38. The dietary supplement of claim 37, wherein a total serving of the dietary supplement has a weight of about 48 grams and comprises the extract product of *Salacia* in a range of 0.1 grams to 1.0 grams, the extract product of *Lagerstroemea speciosa* in a range of 0.005 grams to 0.03 grams, the extract product of French maritime pine bark in a range of 0.01 grams to 0.5 grams, the extract product of *Pterocarpus marsupium* in a range of 0.5 grams to 5.0 grams, and the extract product of *Syzygium cumini* in a range of 0.2 grams to 3.5 grams.

* * * * *

UNITED STATES PATENT AND TRADEMARK OFFICE
CERTIFICATE OF CORRECTION

PATENT NO.         : 8,114,445 B2                                Page 1 of 1
APPLICATION NO.    : 12/613443
DATED              : February 14, 2012
INVENTOR(S)        : Carl W. Hastings It is certified that error appears in the above-identified patent and that said Letters Patent is hereby corrected as shown below:

At Column 8, line 35, "lingoberry" should be -- lingonberry --.

At Column 9, line 5, "Brussel" should be -- Brussels --.

Signed and Sealed this
Twenty-ninth Day of January, 2013

David J. Kappos
*Director of the United States Patent and Trademark Office*